(12) United States Patent
Zhang

(10) Patent No.: US 8,691,045 B2
(45) Date of Patent: Apr. 8, 2014

(54) POSITIONING DEVICE AND POSITIONING METHOD FOR TWO-SIDED ADHESIVE TAPES

(75) Inventor: Bing-Jun Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/418,371

(22) Filed: Mar. 13, 2012

(65) Prior Publication Data

US 2013/0206334 A1 Aug. 15, 2013

(51) Int. Cl.
*B32B 37/12* (2006.01)
(52) U.S. Cl.
USPC ........... 156/299; 156/378; 156/423; 156/580; 73/827; 73/856
(58) Field of Classification Search
USPC .............. 156/60, 378, 423, 580, 299; 73/827, 73/856
See application file for complete search history.

(56) References Cited

U.S. PATENT DOCUMENTS

| | | | | |
|---|---|---|---|---|
| 5,142,905 A | * | 9/1992 | Ezzo et al. | 73/150 A |
| 7,162,929 B2 | * | 1/2007 | Tandon | 73/827 |
| 8,043,449 B1 | * | 10/2011 | Przybelinski et al. | 156/64 |
| 2004/0177707 A1 | * | 9/2004 | Mansky | 73/862.046 |
| 2013/0120828 A1 | * | 5/2013 | Kato | 359/296 |

FOREIGN PATENT DOCUMENTS

WO   WO 2011142320 A1 * 11/2011

* cited by examiner

*Primary Examiner* — Katarzyna Wyrozebski Lee
*Assistant Examiner* — Margaret Squalls
(74) *Attorney, Agent, or Firm* — Novak Druce Connolly Bove + Quigg LLP

(57) ABSTRACT

A positioning device for positioning a number of two-sided adhesive pieces includes a base, a number of pulling blocks, and a pressing block. The base includes a positioning block defining a number of positioning holes. Each pulling block includes a connecting plate, and a supporting plate protruding out from a top end of the connecting plate. A first surface of each adhesive piece is adhered on a top surface of one of the supporting plate. The connecting plate is received in a corresponding one of the positioning hole. The pressing block is attached to the positioning block. A second surface of each adhesive piece to be adhered to a bottom surface of the pressing block.

6 Claims, 6 Drawing Sheets

# POSITIONING DEVICE AND POSITIONING METHOD FOR TWO-SIDED ADHESIVE TAPES

BACKGROUND

1. Technical Field

The present disclosure relates to a positioning device and a positioning method for two-sided adhesive tapes.

2. Description of Related Art

Currently, a method of measuring adhesive strength of a two-sided adhesive tape includes the following steps: cutting the adhesive tape into a number of pieces, adhering a first surface of each adhesive piece on a pulling block, manually adhering a second surface of the adhesive piece on a positioning block, and pressing the pulling block with a predetermined pressure for a predetermined time. However, manually adhering the adhesive piece is usually inaccurate and time-consuming, which cannot satisfy mass-production demands.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, all the views are schematic, and like reference numerals designate corresponding parts throughout the several views.

DETAILED DESCRIPTION

The present disclosure, including the accompanying drawings, is illustrated by way of examples and not by way of limitation. It should be noted that references to "an" or "one" embodiment in this disclosure are not necessarily to the same embodiment, and such references mean at least one.

Figure 1:
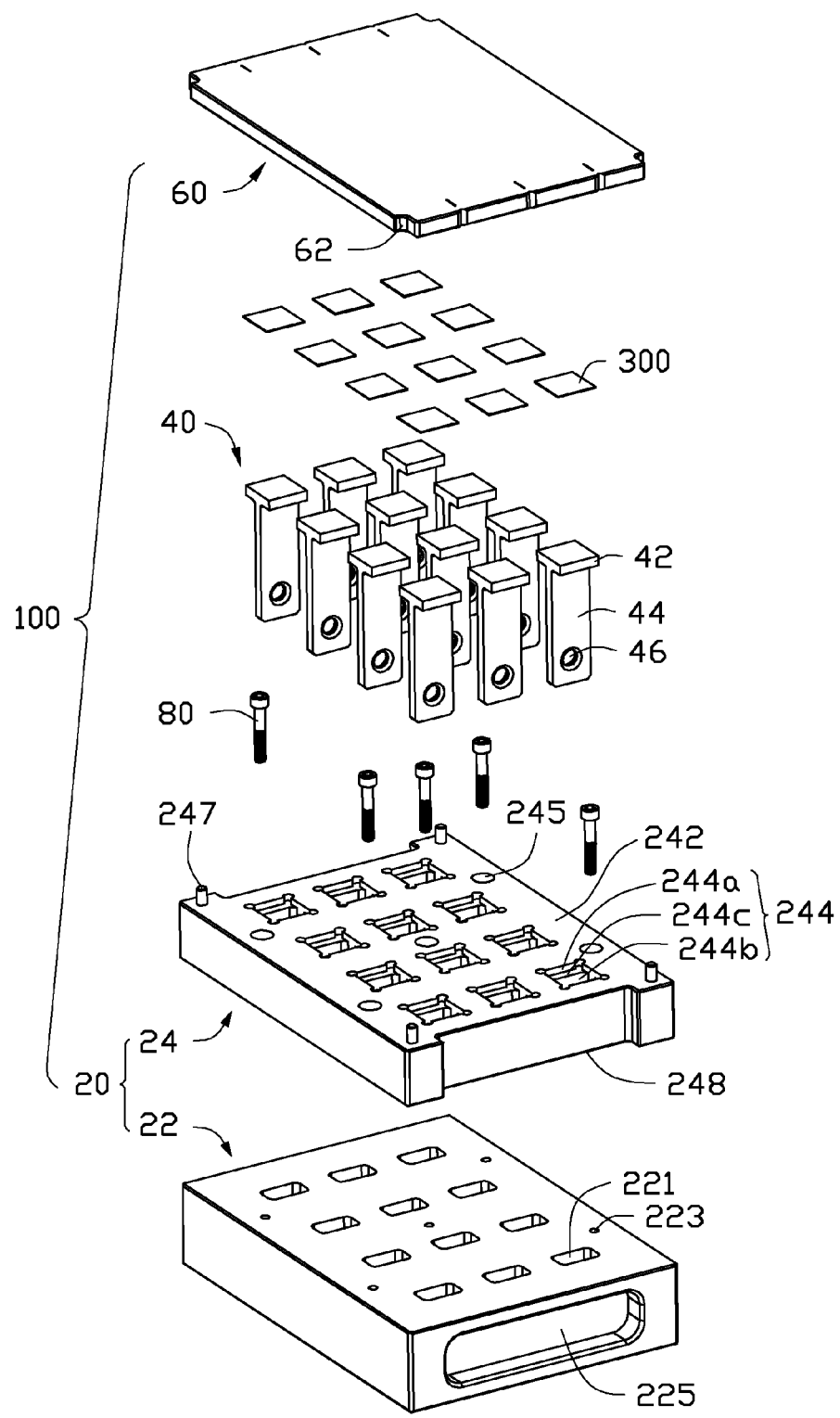
FIG. 1 is an exploded, isometric view of an exemplary embodiment of a positioning device and a plurality of two-sided adhesive pieces.
Figure 2:
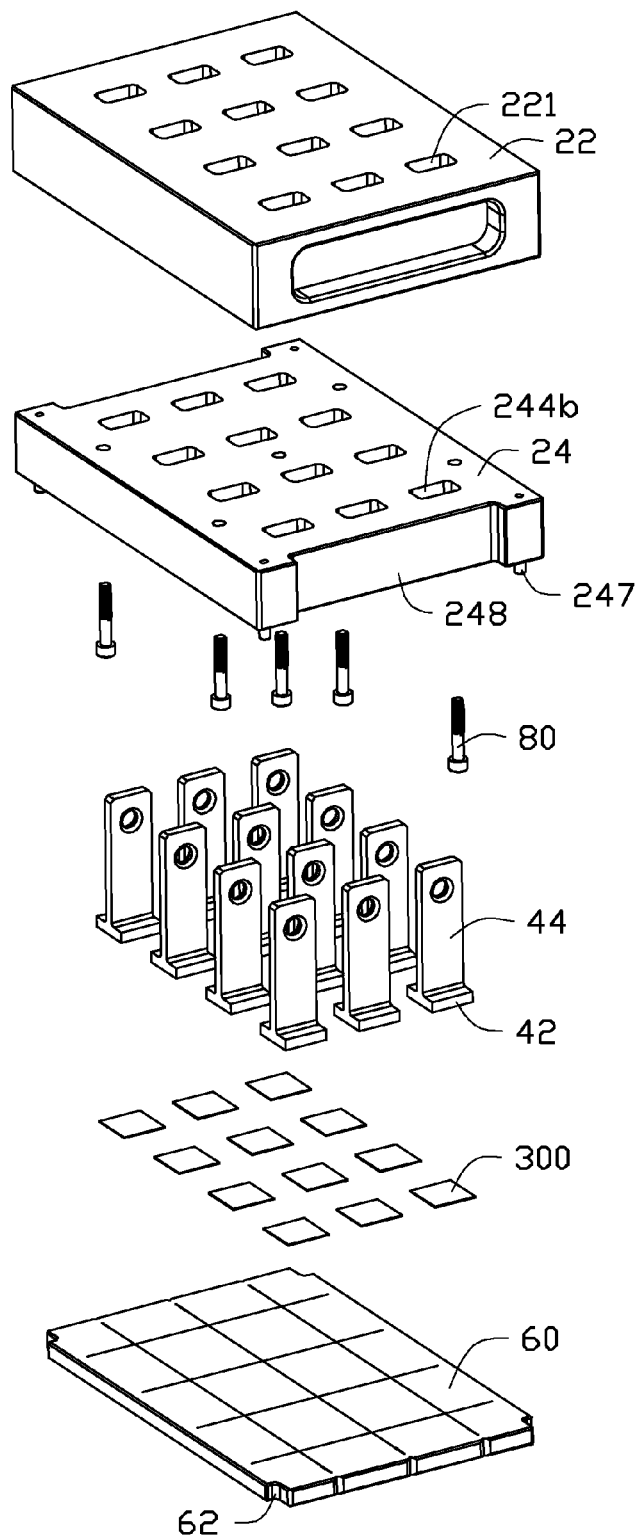
FIG. 2 is an inverted view of FIG. 1.

Referring to FIGS. 1 and 2, an exemplary embodiment of a positioning device 100 for positioning a plurality of two-sided adhesive pieces 300 cut from a two-sided adhesive tape includes a base 20, a plurality of pulling blocks 40, a rectangular pressing block 60, and a plurality of fasteners 80, such as screws 80.

The base 20 includes a rectangular bottom block 22 and a rectangular positioning block 24. The positioning block 24 is made of soft material, such as plastic or rubber. A top surface of the bottom block 22 defines a plurality of through holes 221, and defines a plurality of screw holes 223 in two opposite sides of the top surface. Two recessed portions 225 are defined in two opposite end surfaces of the bottom block 22.

The positioning block 24 is similar to the bottom block 22 in shape. The positioning block 24 includes a rectangular top surface 242. The top surface 242 defines a plurality of positioning holes 244 having same arrangement with the through holes 221, and a plurality of stepped holes 245 having same arrangement with the screw holes 223. Four positioning posts 247 extend up from four corners of the top surface 242. Two opposite end surfaces of the positioning block 24 each define a cutout 248. Each positioning hole 244 includes a receiving portion 244a defined in the top surface 242, and an avoiding portion 244b defined in a bottom surface of the receiving portion 244a through a bottom surface of the positioning block 24. A remained part of the bottom surface of the receiving portion 244a beside the avoiding portion 244b forms a supporting portion 244c.

Each pulling block 40 is substantially T-shaped, and includes a rectangular supporting plate 42 and a connecting plate 44 substantially perpendicularly extending down from a middle of the supporting plate 42. A distal end of the connecting plate 44 opposite to the supporting plate 42 defines a connecting hole 46. A thickness of the supporting plate 42 is slightly larger than a depth of the receiving portion 244a of the positioning block 24.

The pressing plate 60 is similar to the positioning block 24 in shape. Four corners of the pressing plate 60 each define a cutout 62.

Figure 3:
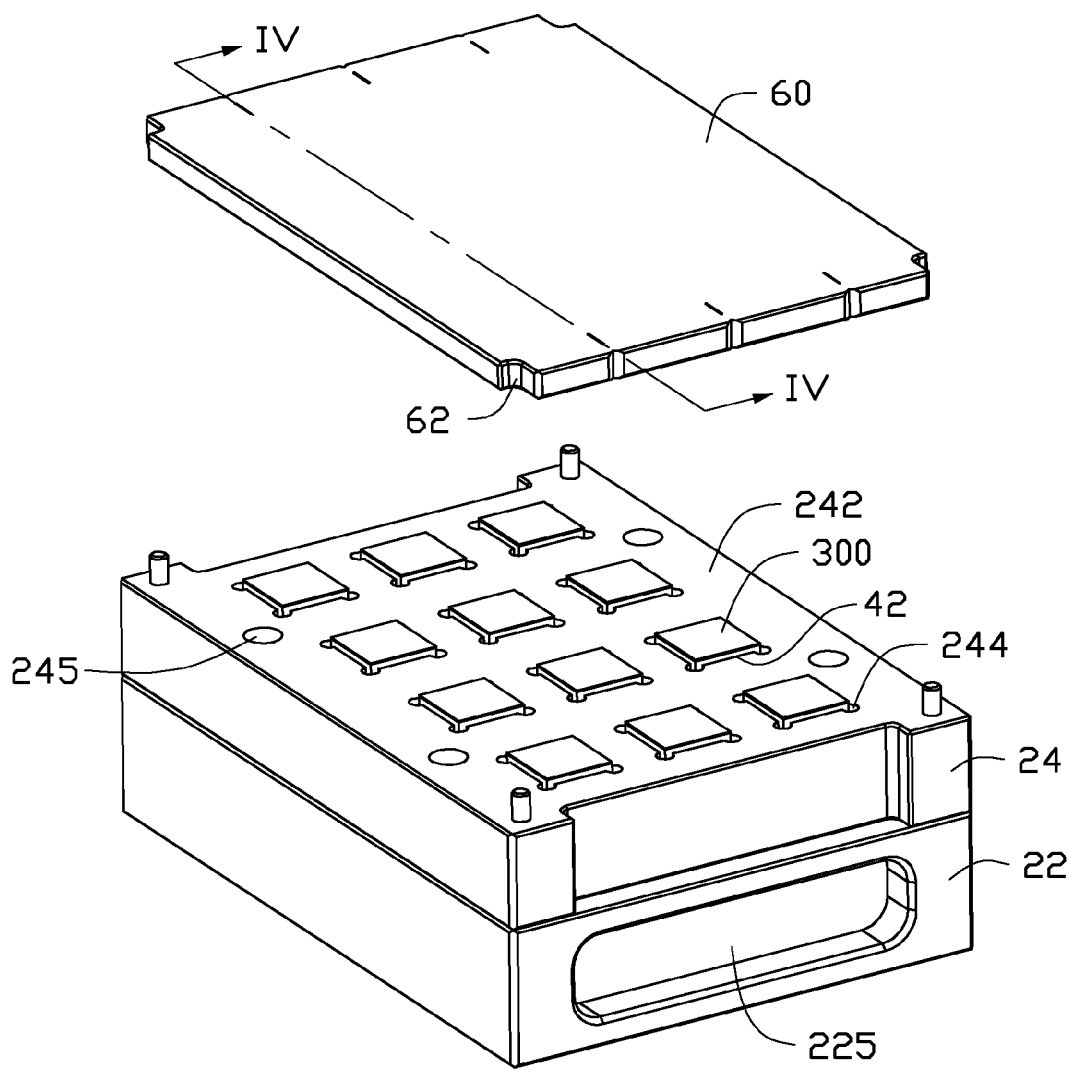
FIG. 3 is a partially assembled, isometric view of FIG. 1.
Figure 4:
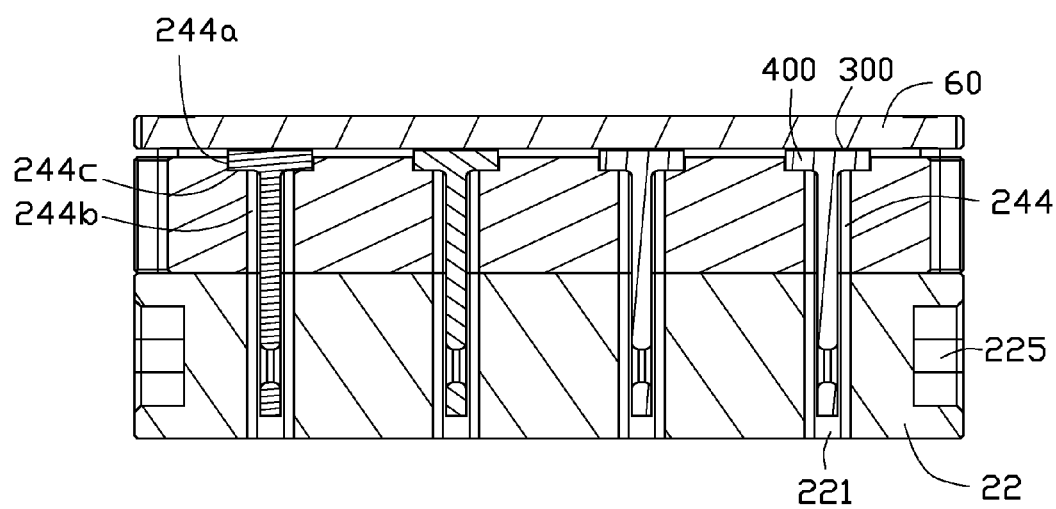
FIG. 4 is a cross-sectional, assembled view of FIG. 3, taken along the line of IV-IV.

Referring to FIGS. 3-4, in assembly, the positioning block 24 is supported on the bottom block 22. The screws 80 extend through the corresponding stepped holes 245 from the top surface 242, to be screwed into the corresponding screw holes 223 of the bottom block 22. The avoiding portions 244b of the positioning holes 244 align with the corresponding through holes 221 of the bottom block 22.

In use, a first surface of each adhesive piece 300 is adhered on a top surface of the corresponding supporting plate 42, opposite to the connecting plate 44. The connecting plate 44 of each pulling block 40 is inserted into the corresponding positioning hole 244 to be received in the avoiding hole 244b of the positioning block 24 and the corresponding through hole 221 of the bottom block 22. Each supporting plate 42 is supported on the corresponding supporting portion 244c. The pressing block 60 is supported on the top surface 242. The positioning posts 247 are inserted into the corresponding cutouts 62. Because the thickness of the supporting plate 42 is slightly larger than the depth of the receiving portion 244a of the positioning block 24, the adhesive pieces 300 are sandwiched between the pressing block 60 and the supporting plates 42, and the adhesive pieces 300 are adhered to the bottom surface of the pressing block 60. The pressing block 60 is pressed by a predetermined pressure for a predetermined time. The fingers of a user can expediently operate the positioning device 100 through the recessed portions 225 of the positioning block 22 to move the positioning device 100. The fingers of the user can also expediently operate the pressing block 60 through the cutouts 248 to remove the pressing block 60 from the positioning block 24.

Figure 5:
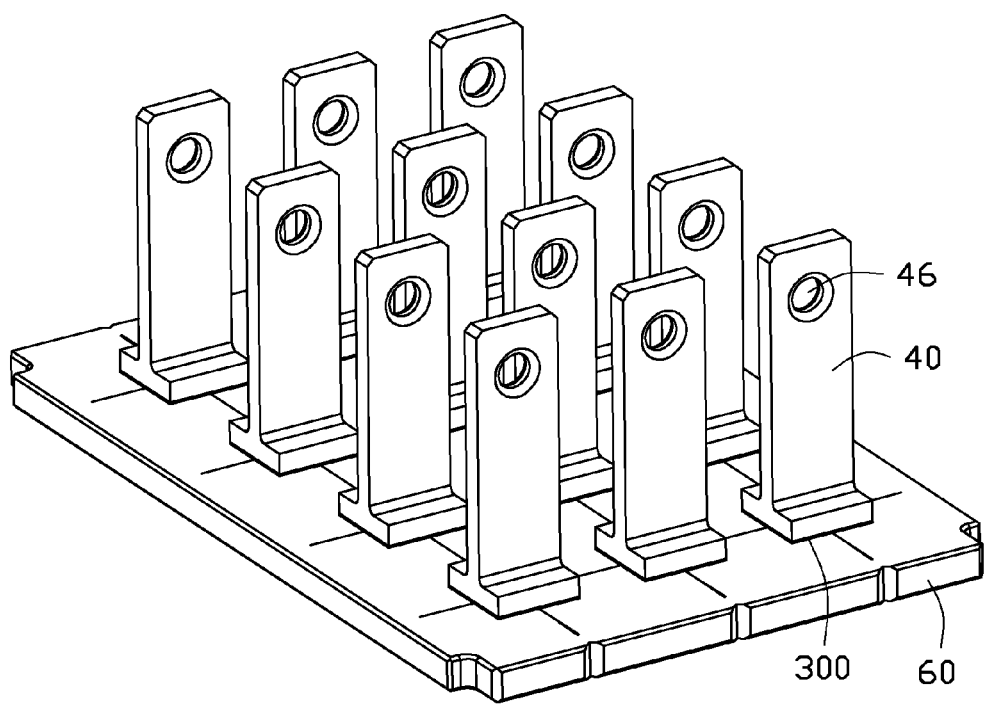
FIG. 5 is a partially assembled, isometric view of FIG. 2.

Referring to FIG. 5, after the predetermined time, the pressing block 60 is pulled up to move away from the positioning block 24. Each pulling block 40 is adhered on the pressing block 60 through the corresponding adhesive piece 300. The pressing block 60 is inverted. The pulling blocks 40 are supported on the pressing block 60. Each pulling block 40 is connected to a test device through the connecting hole 46 to be pulled up to disengage from the pressing block 60, for measuring an adhesive strength of each adhesive piece 300.

Figure 6:
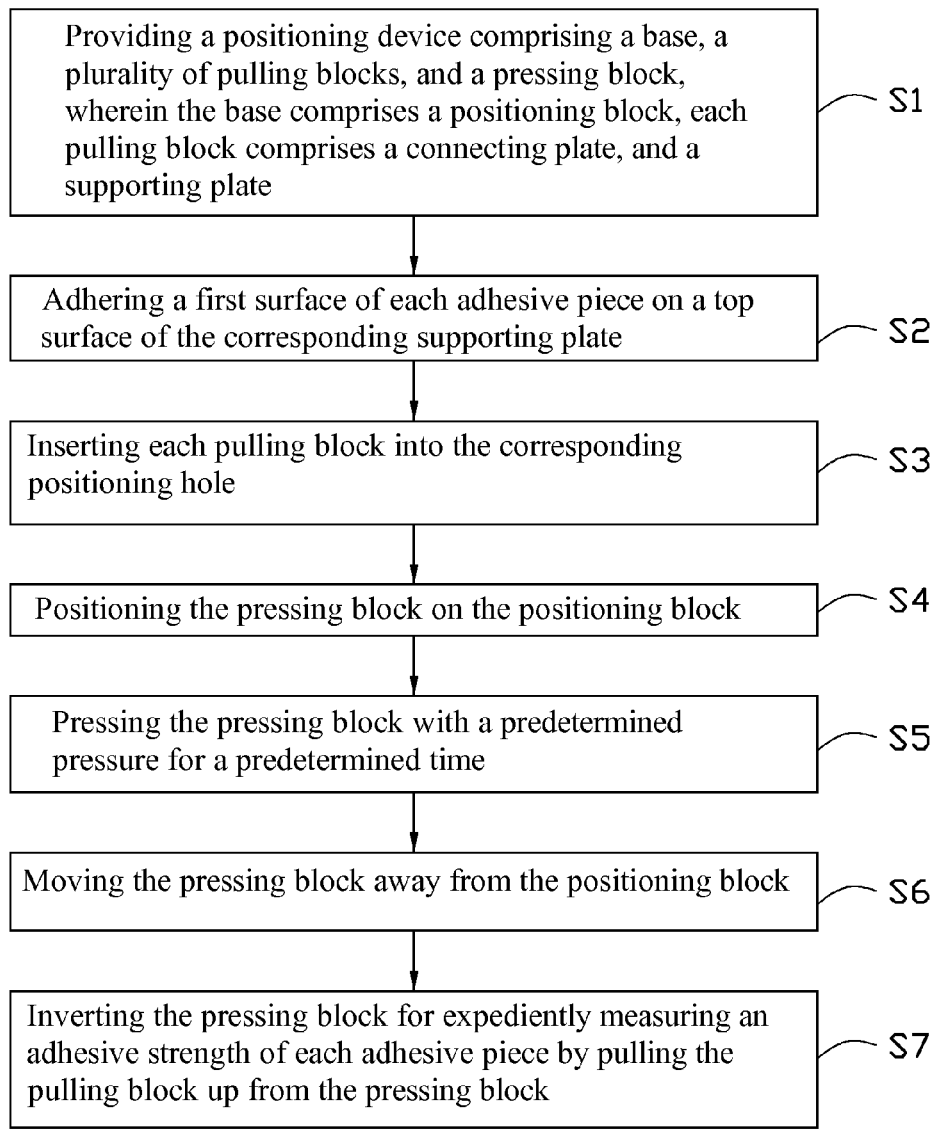
FIG. 6 is a flowchart of one embodiment of a positioning method for positioning adhesive pieces.

Referring to FIG. 6, an embodiment of a positioning method includes steps as follows.

In step 1, a positioning device 100 as described above and a number of two-sided adhesive pieces 300 are provided.

In step 2, each adhesive piece 300 is adhered on a top surface of a corresponding supporting plate 42 with a first surface.

In step 3, each pulling block 40 is inserted into a corresponding positioning hole 244, with each adhesive piece 300 exposed out of the corresponding positioning hole 244.

In step 4, the pressing block 60 is positioned on the positioning block 24, to sandwich the adhesive pieces 300 with the corresponding supporting plates 42, thus a second surface of each adhesive piece 300 adhered to a bottom surface of the pressing block 60.

In step 5, the pressing block 24 is pressed toward the positioning block 24 with a predetermined pressure for a predetermined time.

In step 6, the pressing block 24 is moved away from the positioning block 24, with each pulling block 40 adhered on a bottom surface of the pressing block 60 by the corresponding adhesive piece 300.

In step 7, the pressing block 60 is inverted, with each pulling block 40 supported on the pressing block 60, thus an adhesive strength of each adhesive piece 300 can be measured by pulling the block 40 up from the pressing block 60.

Even though numerous characteristics and advantages of the embodiments have been set forth in the foregoing description, together with details of the structure and function of the embodiments, the present disclosure is illustrative only, and changes may be made in details, especially in the matters of shape, size, and arrangement of parts within the principles of the embodiments to the full extent indicated by the broad general meaning of the terms in which the appended claims are expressed.

What is claimed is:

1. A positioning device for positioning a plurality of two-sided adhesive pieces, the positioning device comprising:

a base comprising a positioning block defining a plurality of positioning holes;

a plurality of pulling blocks each comprising a connecting plate received in a corresponding one of the positioning holes, and a supporting plate protruding out from a top end of the connecting plate, wherein a first surface of each adhesive piece is adhered on a top surface of one of the supporting plates; and a pressing block attached to the positioning block to sandwich the adhesive pieces with the supporting plates of the pulling blocks, a second surface of each adhesive piece to be adhered to a bottom surface of the pressing block;

wherein each positioning hole comprises a receiving portion defined in a top surface of the positioning block for receiving the corresponding supporting plate, an avoiding portion defined in a first part of a bottom surface of the receiving portion for receiving the corresponding connecting plate, and a supporting portion formed on a second part of the bottom surface of the receiving portion for supporting the supporting plate.

2. The positioning device of claim 1, wherein two opposite positioning posts extend up from the top surface of the positioning block, the pressing block defines two cutouts for receiving the corresponding positioning posts.

3. The positioning device of claim 1, wherein the base further comprises a bottom block, the positioning block is supported on the bottom block, the bottom block defines a plurality of through holes aligning with the avoiding portions of the corresponding positioning holes, for receiving the corresponding connecting plates.

4. The positioning device of claim 3, wherein two opposite ends of the bottom block each define a recessed portion for expediently moving the positioning device.

5. The positioning device of claim 1, wherein two opposite ends of the positioning block each define a cutout for expediently removing the pressing block from the positioning block.

6. The positioning device of claim 1, wherein the positioning block is made of plastic or rubber.

* * * * *